United States Patent [19]

Lieberman

[11] Patent Number: 4,807,623
[45] Date of Patent: Feb. 28, 1989

[54] DEVICE FOR SIMULTANEOUSLY FORMING TWO INCISIONS ALONG A PATH ON AN EYE

[75] Inventor: David M. Lieberman, c/o Pfizer Inc., 235 E. 42nd St., New York, N.Y. 10017

[73] Assignee: David M. Lieberman, Montague, N.J.

[21] Appl. No.: 202,223

[22] Filed: Jun. 3, 1988

Related U.S. Application Data

[63] Continuation of Ser. No. 868,973, May 30, 1986, abandoned.

[51] Int. Cl.[4] .............................................. A61B 17/32
[52] U.S. Cl. ..................................... 128/305; 128/310; 30/300; 33/27.01
[58] Field of Search ............... 604/22; 128/305, 305.1, 128/310, 753, 754; 30/50, 300, 301, 310; 33/27.01, 27.12

[56] References Cited

U.S. PATENT DOCUMENTS

| | | | |
|---|---|---|---|
| 2,249,906 | 7/1941 | Longoria | 128/305 |
| 3,628,522 | 12/1971 | Kato | 128/751 |
| 4,205,682 | 6/1980 | Crock et al. | 128/305 |
| 4,298,004 | 11/1981 | Schachar et al. | 128/305 |
| 4,342,951 | 8/1982 | Muller et al. | 318/625 |
| 4,417,579 | 11/1983 | Soloview et al. | 128/303 R |
| 4,423,728 | 1/1984 | Lieberman | 128/310 |
| 4,429,696 | 2/1984 | Hanna | 128/310 |
| 4,520,815 | 6/1985 | Marinoff | 128/303 R |
| 4,526,171 | 7/1985 | Schachar | 128/305 |
| 4,565,198 | 1/1986 | Koeniger | 128/305 |
| 4,593,467 | 6/1986 | Safar | 30/300 |
| 4,718,418 | 1/1988 | L'Esperance, Jr. | 128/303.1 |

FOREIGN PATENT DOCUMENTS

| | | | |
|---|---|---|---|
| 2320380 | 4/1973 | Fed. Rep. of Germany | 128/305 |
| 2493137 | 11/1980 | France | 128/305 |

*Primary Examiner*—Michael H. Thaler
*Assistant Examiner*—William W. Lewis
*Attorney, Agent, or Firm*—Anthony J. Casella; Gerald E. Hespos

[57] ABSTRACT

An ophthalmic device includes a base, a suction ring connected to the base to secure the device to the eye of a patient, and a support piece carrying a pair of securely ganged cutting blades having cutting edges oriented at an angle with respect to one another. The support piece can be raised and lowered with respect to the eye surface, and rotated around the base to simultaneously form two incisions along a path on the eye. The device includes a mechanism for progressively advancing the two cutting blades together in the support piece, while maintaining a constant angular cutting edge relative orientation, to a position in which the cutting points of the two cutting blades are touching, and can thus be used to form an annular wedge-like cut of eye tissue in the treatment of refractive errors. In alternative embodiments, laser or electrosurgical knives may be used instead of cutting blades.

14 Claims, 8 Drawing Sheets

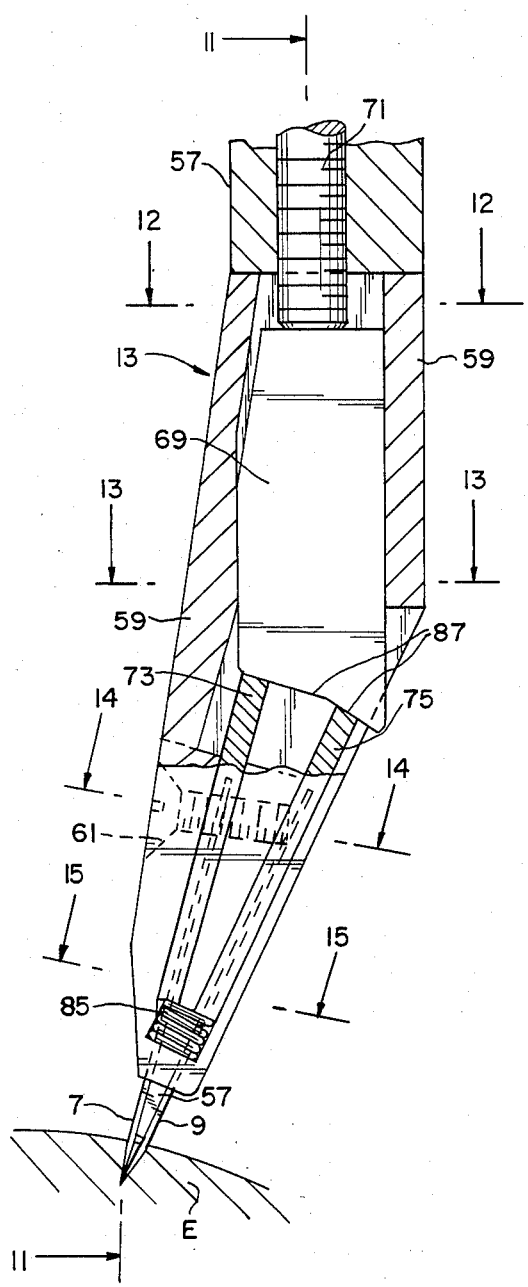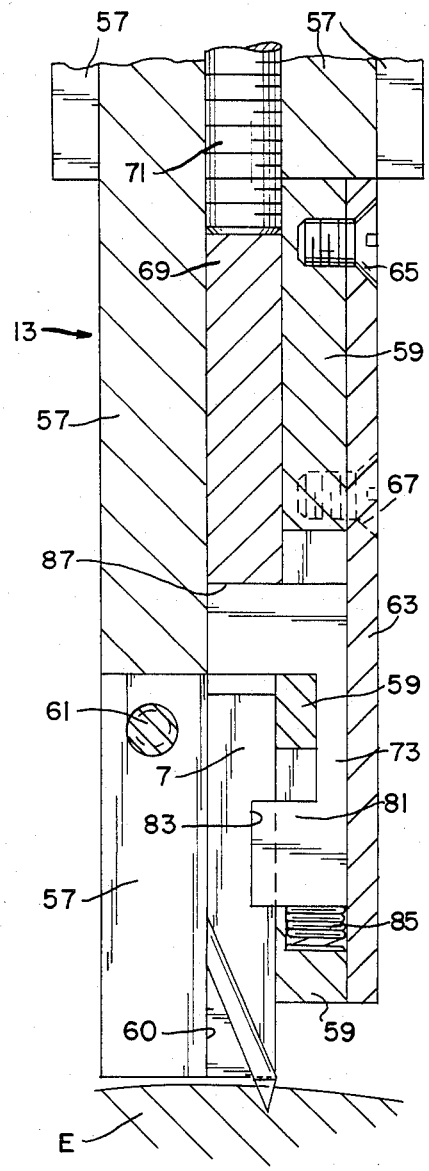
FIG.10
FIG.11

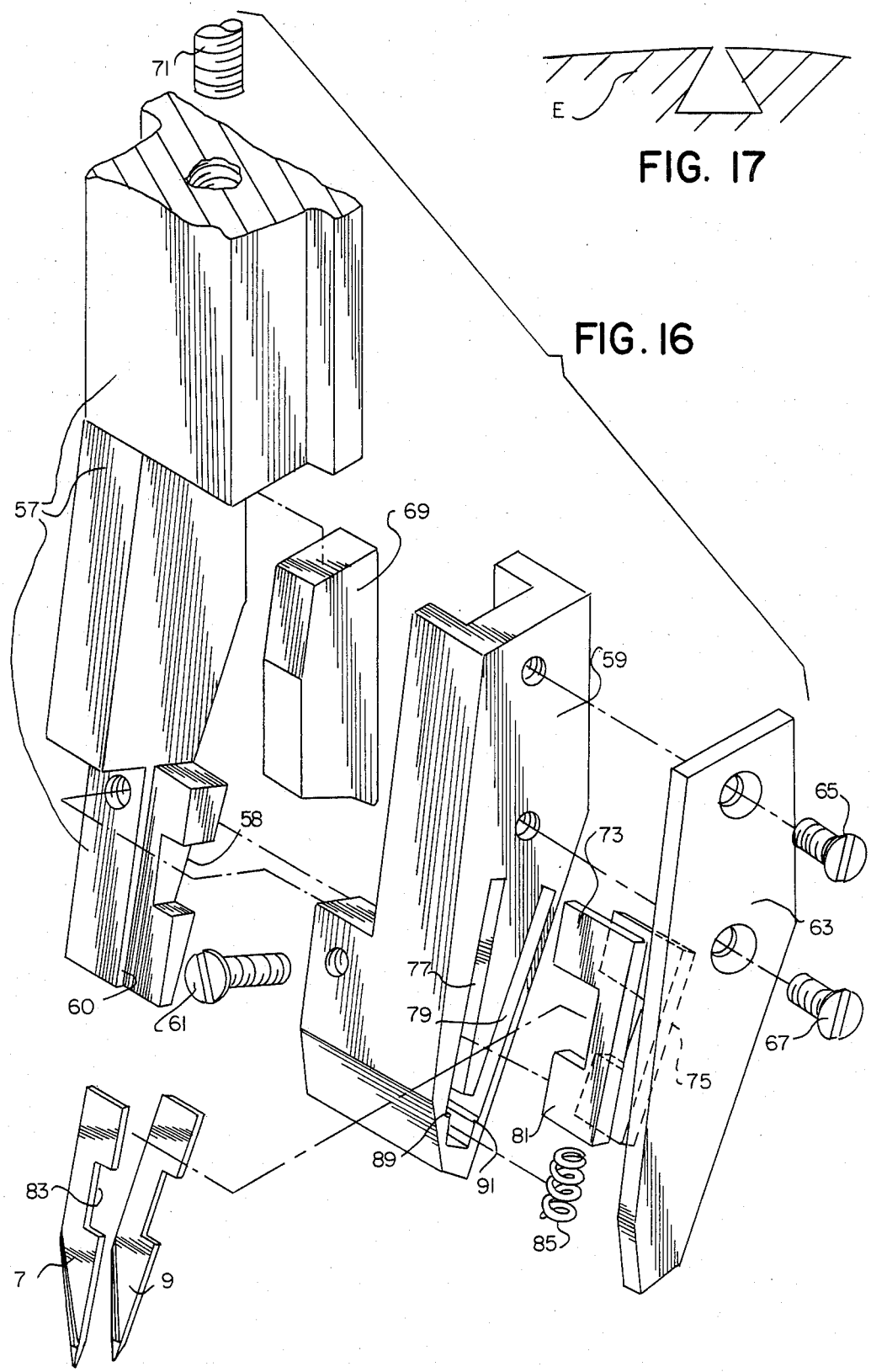

DEVICE FOR SIMULTANEOUSLY FORMING TWO INCISIONS ALONG A PATH ON AN EYE

This application is a continuation of U.S. patent application Ser. No. 868,973 which was filed on May 30, 1986 now abandoned.

BACKGROUND OF THE INVENTION

The present invention is related to the field of keratorefractive surgery (also known as refractive corneal surgery), which involves surgical procedures to alter the shape of the cornea and thereby alter the refractive pattern of light passing through the cornea. A thorough review of keratorefractive surgical procedures is provided by Binder P. S., entitled "Refractive Surgery: Its Current Status and Its Future", in The Contact Lens Association of Ophthalmologists Journal, Vol. 11(4), pp. 358–375 (Oct./Dec. 1985). In particular, the present invention is directed to a surgical instrument for forming incisions in the cornea which is useful, for example, in the treatment of myopia (nearsightedness) or hyperopia (far-sightedness).

Myopia results from physiological imperfections in the eye of a patient which cause the focusing of images in front of the retina. According to the "law of spheres", the human eye can be approximately modeled by a pair of intersecting hollow spheres of different diameter and wall thickness, with the corneal surface being the outer surface of the smaller sphere. Thus, surgical operations to correct myopia have typically involved techniques for effectively flattening the corneal surface in order to cause a posterior displacement of the focal point.

On the other hand, hyperopia results from physiological imperfections causing the focusing of images behind the retina, and a surgical technique intended to correct this condition will necessarily seek to alter the patient's eye so as to achieve an anterior displacement of the focal point.

At the present time, the principal keratorefractive surgical procedure performed (roughly 100,000 procedures annually in the United States) for the correction of myopia is the procedure of Sato, as popularized by Fyodorov and commonly known today as radial keratotomy. In this procedure a series of radial incisions are made in the anterior cornea extending from the edge of the pupil outwardly almost to the limbus. These incisions serve to permanently weaken the cornea so that the effect of the intraocular pressure is to displace the cornea so that the surface of the cornea flattens. However, clinical results with this procedure have been characterized by significant variability of results from patient to patient and an undesirably high level of complications such as under and overcorrection, increased astigmatism, corneal iron lines and epithelial downgrowth into the incisions. The incisions are left open (i.e. unsutured) after surgery and thus can be susceptible to infection. Inadvertent perforation of the cornea can occur in the practice of this procedure; the eye, once opened, must be closed and infection of the internal matter of the eye, possibly leading to permanent and irrevocable loss of vision, can result from a perforation. If the incision is within the pupillary opening, permanent glare may be experienced by the patient.

An alternative keratorefractive surgical procedure for the correction of myopia is disclosed in U.S. Pat. No. 4,423,728. An annular wedge-like cut is made in (but not completely through) the cornea along a 360° path between the pupil and the limbus. The adjacent walls of the cut are sutured together, causing a carefully controlled flattening of the corneal surface without structurally weakening the cornea or exposing the internal content of the eye to infection. The corrective effect progressively increases as the radius of the wedge-like cut is decreased, and thus virtually all degrees of myopia observed clinically are correctable by this technique. The aforementioned patent also discloses a device for forming such an annular wedge-like cut in a patient's eye in which two distinct support pieces carry respectively a first vertically-disposed blade and a second blade oriented at an acute angle with respect to the first blade. The two support pieces are connected to different portions (180° apart) of a platter which rotates upon a base fixed to the eye. The two support pieces, and thus the two cutting blades, are raised and lowered independently of one another.

The use of the device disclosed in U.S. Pat. No. 4,423,728 has proven to be somewhat problematical. The two blades are adjusted independently and it is quite difficult to position the angled blade at the correct diameter (relative to the diameter of the path of the vertical blade) to create a wedge-like cut of the desired depth and thickness. Furthermore, after the first wall of the cut has been formed the corneal tissue exhibits a tendency to deform around the subsequently passing second blade, so that the second blade merely follows the track left by the first blade and does not cut the intended second wall of the wedge-like cut. Finally, the angled cutting blade cannot be made to follow a non-circular path on the patient's eye.

SUMMARY OF THE INVENTION

It is an object of the invention to provide an ophthalmic cutting device which obviates the problems described above associated with the use of the device disclosed in U.S. Pat. No. 4,423,728.

This and other objects of the invention are realized with a novel ophthalmic device for simultaneously forming two incisions oriented at an angle with respect to one another along a path on an eye, which device comprises a base; means connected to the base (for example a suction ring assembly) to conform and secure the eye and the ophthalmic device to one another; first and second cutting means; pattern means operatively coupled to said first and second cutting means for defining said path; rotation means adapted to be disposed and rotated on the base; and means for mounting both the first and second cutting means upon a single portion of the rotation means in such a manner that said two cutting means are securely ganged together with the cutting directions of said two cutting means oriented at an angle with respect to one another, with said mounting means including a means for adjusting the position of said two ganged cutting means with respect to the surface of the eye, whereby when the position of the two ganged cutting means is appropriately adjusted and the rotation means is rotated on the base, the two cutting means simultaneously cut said two incisions while following said path on the eye defined by the pattern means. It is usually preferred that the first and second cutting means be mounted upon the rotation means in such a manner that the distance between the locus of tissue being cut by the first cutting means and the locus of tissue being cut at the same time by the second cutting means is substantially equal to the distance between the two incisions being simultaneously cut, which in essence means that when the cutting means comprise cutting blades, the two blades are held together in a close side-by-side relationship. It is possible, however, for one cutting blade to have a leading cutting position to a certain extent with respect to the other blade (which therefore is in a trailing position) as the rotation means is rotated, e.g. in a surgical technique to correct for hyperopia.

The pattern means may comprise a generally annular cam operatively connected to the base, as in the case of the device disclosed in U.S. Pat. No. 4,423,728, or may alternatively comprise another type of mechanical, electrical or computer-guided control system. An important aspect of the present invention is that the pattern means positively defines the single path simultaneously followed on the patient's eye by both incisions. Usually, this path is predetermined (e.g. by the shape of an annular cam or by a computer program) prior to the commencement of the formation of the two incisions, but it is contemplated that the pattern means may include a feedback loop capable of altering the incision path as the cutting operation is in progress. The first and second cutting means may each comprise, for example, a laser knife (preferably connected to an ultraviolet wavelength excimer laser source), a heated electrosurgical knife or a cutting blade, with cutting blades being preferred at the present time.

In a preferred type of device of the invention, each of the first and second cutting means comprises a cutting blade having a cutting edge terminating at a cutting point, said cutting blades being securely ganged together with said cutting edges oriented at an acute angle with respect to one another, and the cutting blades mounting means comprises (1) a means for adjusting the position of the two ganged cutting blades with respect to the surface of the patient's eye without effecting a relative movement between said two blades and (2) a means for simultaneously and progressively advancing the two ganged cutting blades, while maintaining the two cutting edges oriented at said acute angle with respect to one another, to a position in which said cutting points are touching one another. By repeatedly passing the ganged cutting blades over the path on the patient's eye and progressively advancing the angled blades for each pass, the two incisions can be made to form a wedge-like cut of eye tissue along said path. An important advantage of this preferred embodiment is that the depth of the wedge-like cut is strictly limited by the inability to progressively advance the two cutting blades beyond the position in which their cutting points are touching. The device can thus be readily designed so that the wedge-like cut will extend only partially across the corneal wall and not through Descemet's membrane.

DETAILED DESCRIPTION OF THE INVENTION

The invention will be described in detail with reference to a preferred embodiment thereof, which is an ophthalmic device for forming a 360° wedge-like cut in the cornea in a surgical procedure for the correction of myopia. In the drawings:

FIG. 10 is an enlarged sectional view in the plane of FIGS. 2 and 4 of the lowermost portion of the cutting blade support piece, with the two cutting blades fully advanced within the support piece to a position in which their two cutting points are touching;

FIGS. 11 to 15 are sectional views taken along lines 11—11, 12—12, 13—13, 14—14 and 15—15, respectively, of FIG. 10;

FIG. 16 is an exploded perspective view of the support piece (lowermost portion only shown) and cutting blades of the device of FIG. 1; and FIG. 17 is a transverse cross-sectional view of a 360° closed generally annular wedge-like cut formed by a cutting device of the invention in a surgical procedure for the correction of hyperopia.

Figure 1:
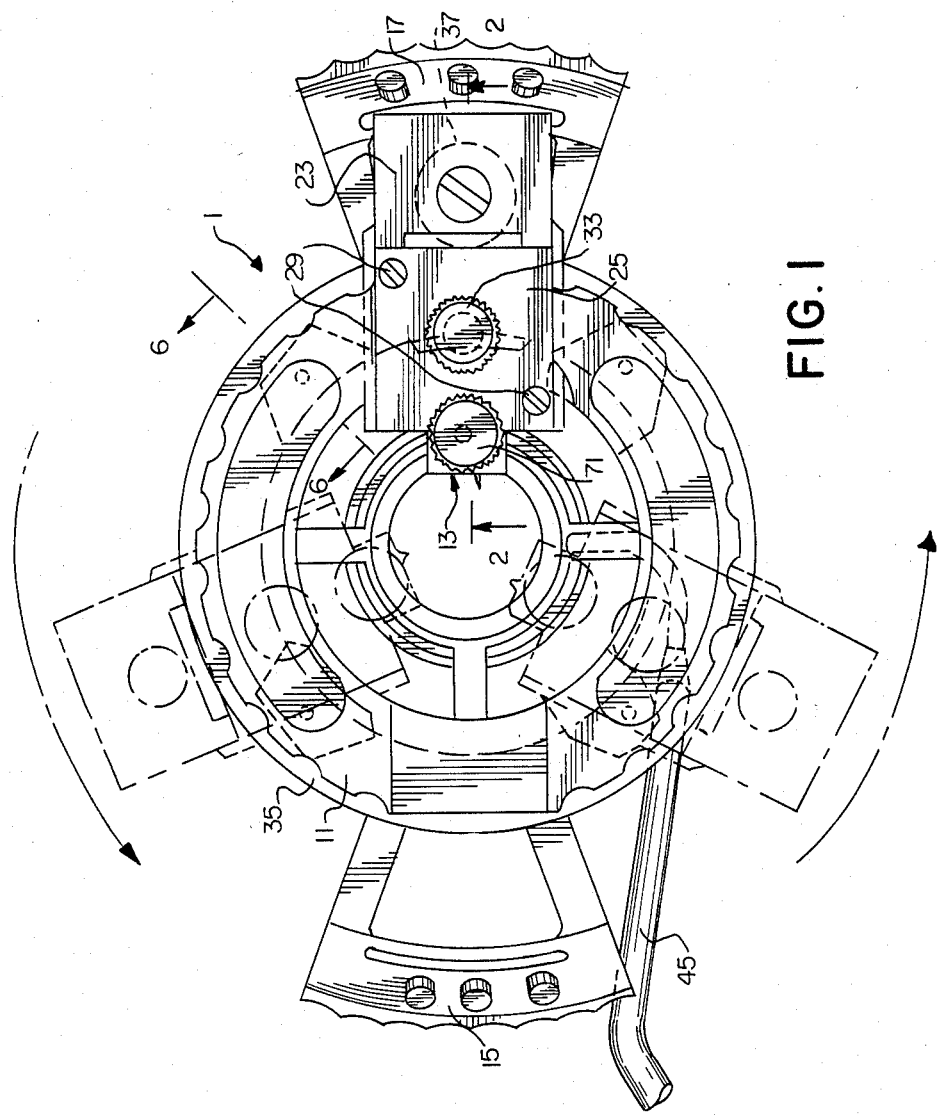
FIG. 1 is a top plan view of an ophthalmic cutting device of the invention, with various positions of the cutting blade support piece assumed during the rotation of the platter of the device upon the base fixed to the patient's eye shown in phantom.

An ophthalmic cutting device 1 of the invention is illustrated in FIGS. 1 to 8 and 10 to 16. Device 1 includes a suction ring 3 for conforming and securing the patient's eye E and device 1 to one another, an annular base 5 integral with the suction ring 3, first and second cutting blades 7 and 9, a platter 11 mounted and rotatable upon the base 5, and a cutting blade support piece 13 mounted upon platter 11. The base 5 includes a pair of finger grips 15 and 17. In the device shown in the figures, suction ring 3 and base 5 are connected by an outer cone 19, and elements 3, 5 and 19 make up a unitary one-piece article. Platter 11 includes an inner cone 21 which fits and rotates within the outer cone 19.

Figure 5:
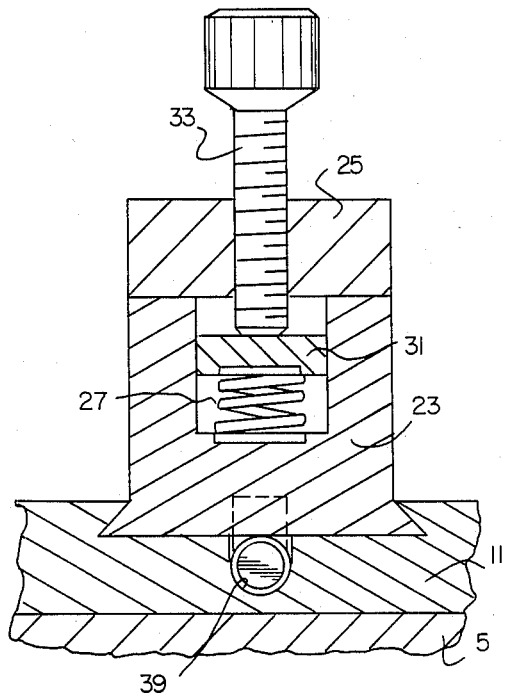
FIG. 5 is a sectional view taken along line 5—5 of FIG. 4.

Support piece 13, which carries blades 7 and 9, is mounted on the rotating platter 11 by means comprising two blocks 23 and 25 and a compression spring 27. As is shown in FIG. 5, block 23 is received in a sliding dovetail fit within platter 11. The upper and lower mounting blocks 25 and 23 are securely affixed together, for example with a plurality of screws 29, and are dimensioned to define between themselves a space into which spring 27 and an elongated terminal portion 31 of support piece 13 are fitted (see FIG. 5). Support piece 13 is fit into mounting block 23 in the manner shown in FIG. 3, and mounting block 23 includes a vertical depending shelf 42 to stabilize support piece 13 against any tendency to wobble in the plane of FIGS. 2 and 4. A first threaded adjustment screw 33 is provided in a threaded bore in the upper mounting block 25, with the lower free end of screw 33 (opposite the screw head) contacting the upper surface of support piece portion 31 at a location directly above compression spring 27. Spring 27 continuously urges portion 31 against the lower free end of screw 33. The vertical position of the cutting blades 7 and 9 can be readily adjusted with respect to the surface of the eye, without effecting any relative movement between blades 7 and 9, by rotating the adjustment screw 33 so as to raise or lower that screw and support piece portion 31, as is illustrated in FIGS. 2 and 4.

Figure 2:
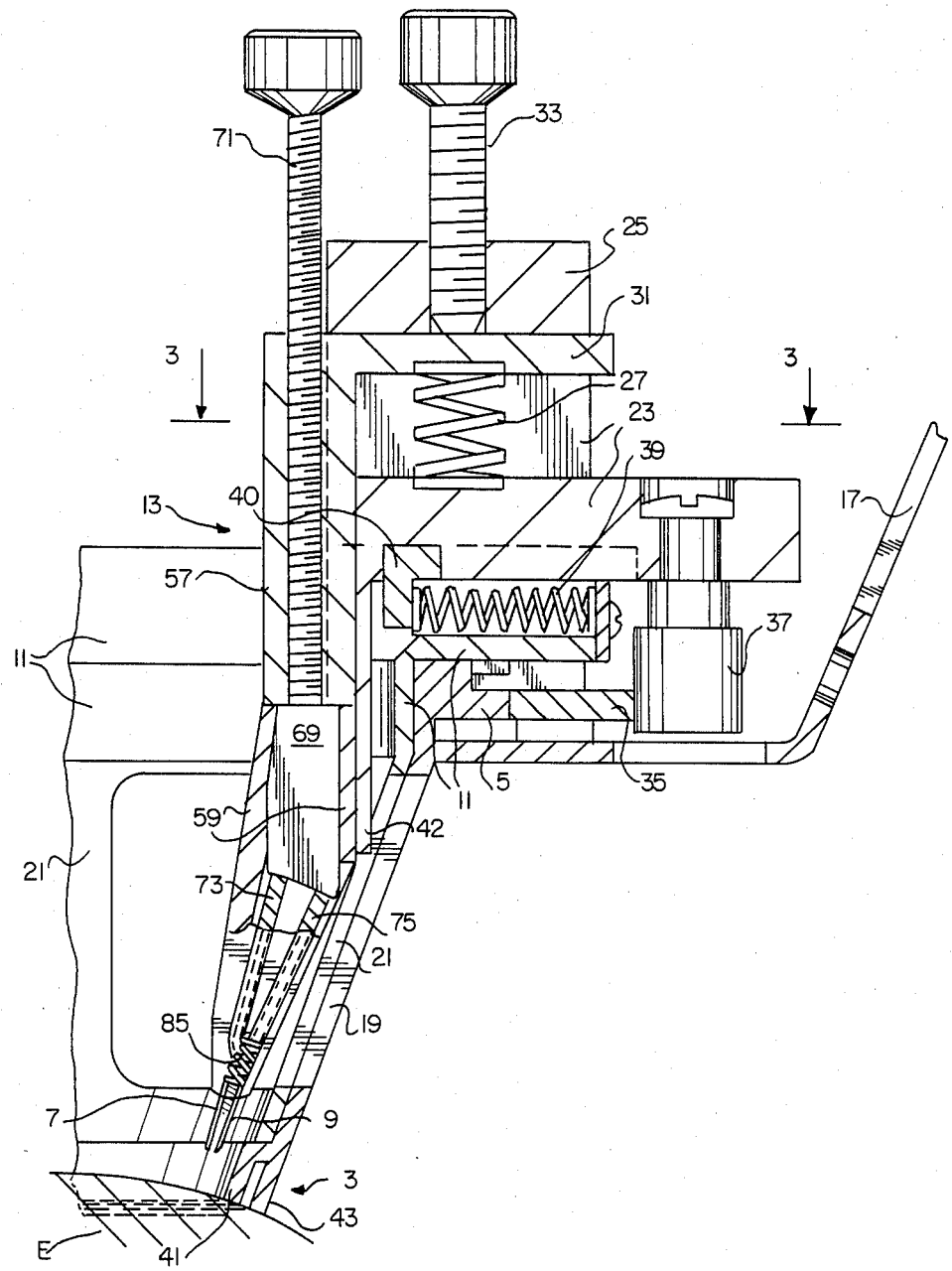
FIG. 2 is a sectional view taken along line 2—2 in FIG. 1, with the two cutting blades raised above the surface of the patient's eye.
Figure 3:
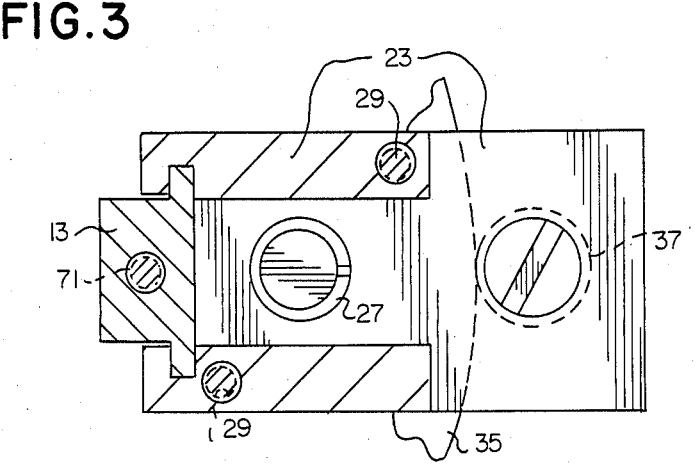
FIG. 3 is a sectional view taken along line 3—3 in FIG. 2.
Figure 4:
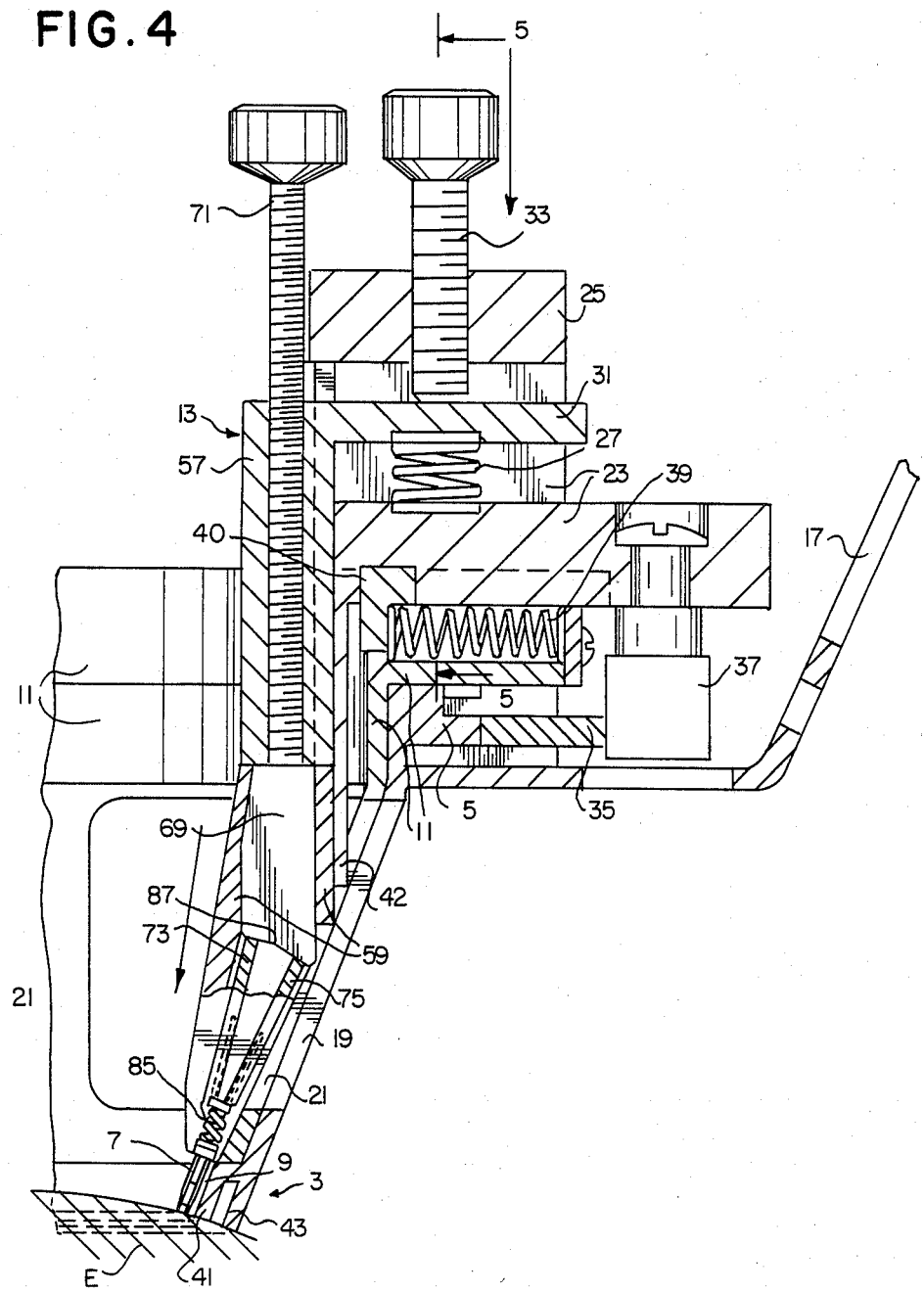
FIG. 4 is the same sectional view as in FIG. 2, but with the cutting blades lowered together so that their two cutting points are just touching the eye surface.
Figure 6:
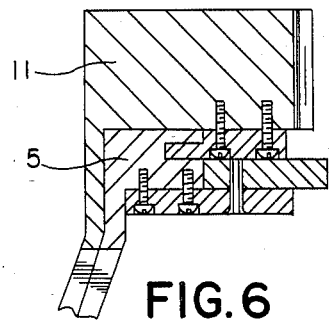
FIG. 6 is a sectional view taken along line 6—6 of FIG. 1.

Device 1 also includes a stationary annular master cam 35 removably secured to base 5, a slave cam 37 carried by lower mounting block 23, and a pre-loaded compression spring 39 (abutting pin 40 rigidly secured to block 23) that continuously urges block 23 (and thus also block 25 and support piece 13) inwardly in the device (i.e. to the left in FIGS. 2 and 4). The slave cam 37 thus continuously rides against the stationary master cam 35 and the path followed by cutting blades 7 and 9 along the eye of a patient, which path may be either circular or non-circular, is positively and directly determined by the peripheral configuration of the master cam 35. If desired, the shape of the path followed by blades 7 and 9 can be readily altered simply by replacing the master cam with another master cam having an appropriate peripheral configuration.

Suction ring 3 of device 1 functions by virtue of the void space left between inner and outer suction rings 41 and 43, which void space communicates with a tube 45 adapted to be connected to a source of suction. Suction ring 3 may be identical to the one in the cutting device disclosed in the aforementioned U.S. Pat. No. 4,423,728, and accordingly may have a frustoconical shape with a constant height throughout. It is also contemplated that the suction ring may be slightly tilted in such a way that its height varies between maximum and minimum values at about 180° opposed locations in order to compensate for the variation in corneal thickness between the inferior (minimum corneal thickness) and superior (maximum corneal thickness) cornea. Appropriate indexing means should also be provided so that the surgeon can readily position the maximum height location of the suction ring upon the inferior cornea. In this way the depth of the incisions made by the two cutting blades will be smallest where the cornea is thinnest and largest where the cornea is thickest, but the separation of the bottoms of the incisions from the Descemet's membrane at the inner corneal wall will remain substantially constant throughout the incisions.

Figure 7:
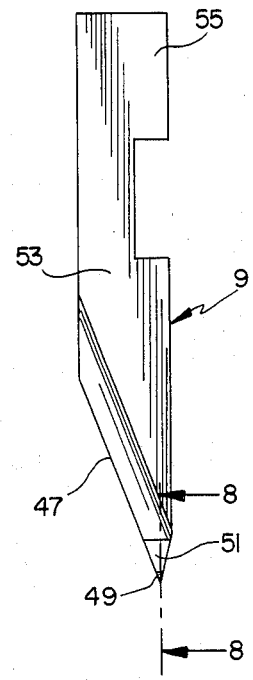
FIG. 7 is a side plan view of one of the cutting blades in the device of FIG. 1.
Figure 8:
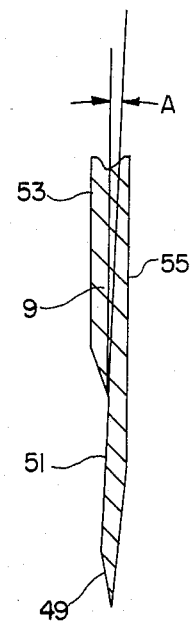
FIG. 8 is a sectional view taken along line 8—8 of FIG. 7.

One of the two cutting blades, i.e. cutting blade 9, is depicted in FIGS. 7 and 8. Blade 9 has a cutting edge 47 which terminates at a cutting point 49. As shown in FIG. 8 a relieved surface 51 is provided adjacent to point 49 on the side of the blade (the left side in the view of FIG. 8) intended to face blade 7. Surface 51 makes an angle A of about 2° with the parallel side faces 53 and 55 of the main body of blade 9. Blade 7 is identical to blade 9 except that the relieved surface is provided on the right side of the blade (looking in the same direction as FIG. 8), which is intended to face blade 9. The presence of the opposed relieved surfaces on cutting blades 7 and 9 enables the cutting points of these two blades to come into contact without interference when the cutting edges of the two blades are mutually oriented at a small acute angle, for example about 7°.

The lowermost portion of the cutting blade support piece 13 is shown in FIGS. 10, 11 and 16. As is best shown in FIG. 16, support piece 13 includes a body piece 57 (which in turn includes elongated portion 31), an end piece 59 secured to piece 57 by means of a threaded screw 61, a cover piece 63 secured to piece 59 by means of threaded screws 65 and 67, a pusher block 69 which fits within a channel defined between pieces 57 and 59, and a second threaded adjustment screw 71 received in a threaded bore in the body piece 57. Guide blocks 73 and 75 are carried in a close sliding fit within a pair of mutually angulated slots 77 and 79 defined in end piece 59, with guide block 73 in slot 77 and guide block 75 in slot 79. As is best shown in FIGS. 11 and 16, the cutting blades 7 and 9 are engaged to the guide blocks with a lower portion of each guide block, e.g. portion 81, fitting into a recess, e.g. recess 83, provided in the respective cutting blade, e.g. blade 7. Blades 7 and 9 are carried in a close sliding fit within a pair of thin slots defined between body piece 57 and end piece 59. The relative angulation between these two thin slots (which is the same as the relative angulation between slots 77 and 79) positively establishes the fixed relative angulation between the cutting edges of the ganged cutting blades 7 and 9 of the device 1. Blade 7 rides against one side of body piece 57 and against a ledge 60 (having the same thickness as blade 7) provided on that side of piece 57, while blade 9 rides against the other side of body piece 57 (not visible in FIG. 16) and against a ledge thereon identical to ledge 60. A compression spring 85 held between end piece 59 and the two lower portions (e.g. portion 81) of the cutting blade guide blocks 73 and 75 continuously urges blocks 73 and 75 against the lower surface 87 of the pusher block 69. In its turn, pusher block 69 is continuously urged by the action of spring 85 against the lower free end (opposite the screw head) of adjustment screw 71. By rotating the adjustment screw 71 so as to raise or lower that screw and pusher block 69, cutting blades 7 and 9 (which extend through the lower end of end piece 59) can readily be simultaneously and progressively advanced towards or retracted away from a relative position in which the cutting points of the two blades are touching one another, all the while maintaining the two cutting edges of the blades at the same fixed acute angle relative to one another. A notch 58 is provided in body piece 57 to provide clearance for said two lower portions (e.g. portion 81) of guide blocks 73 and 75. Also, shoulders 89 and 91 in end piece 59 serve as stops for guide blocks 73 and 75 when the two blade cutting points have reached the touching position. Preferably (see FIG. 10), lower surface 87 of pusher block 69 is provided with two portions mutually angulated at approximately said fixed acute angle, one of which portions contacts block 73 and the other of which portions contacts block 75. It is also preferred that body piece 57 extend below end piece 59 and cover piece 63 (see FIG. 11) to enhance the stabilization of the cutting blades 7 and 9.

The various individual pieces and parts of which device 1 is comprised may be prepared by conventional methods, for example casting, machining, etc., from a suitable metal or metal alloy (e.g. stainless steel). Alternatively, injection molded plastic pieces and parts may be utilized in a disposable embodiment of the invention.

Figure 9:
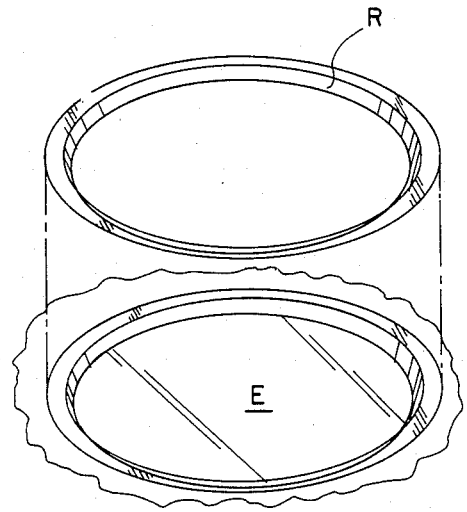
FIG. 9 is a perspective view showing the annular wedge-like ring of corneal tissue that is removed from the patient's eye by the device of FIG. 1 during a surgical procedure for the correction of myopia.
Figure 12:
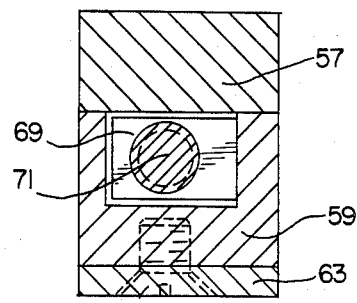
Figure 13:
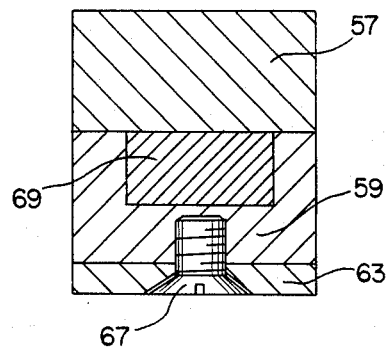
Figure 14:
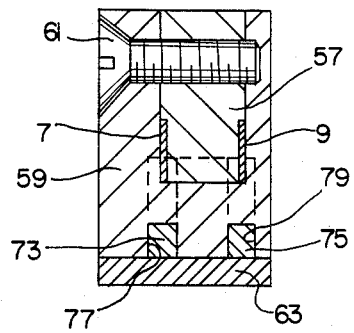
Figure 15:
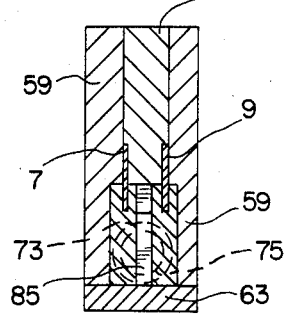

The operation of cutting device 1 will be described with reference to an ophthalmic surgical procedure for the correction of myopia. With screws 33 and 71 adjusted so that terminal portion 31 and pusher block 69 are in their highest positions (with portion 31 abutting mounting block 25 and the upper surface of pusher block 69 abutting body piece 57 as shown in FIG. 2), suction ring 3 is secured to the eye E of a patient at an appropriate disposition on the eye. Adjustment screw 33 is then rotated to lower support piece 13 to a position (shown in FIG. 4) in which the two cutting blades, which are lowered as a ganged unit, are just touching the surface of the eye. The surgeon then holds finger grips 15 and 17 with the fingers of one hand and rotates platter 11 with the fingers of the other hand to begin forming the two incisions. After each full turn of the platter 11, the adjustment screw 71 is rotated to slightly lower the pusher block 69 and thus slightly advance the angulated cutting blades 7 and 9. Eventually the cutting blade disposition shown in FIG. 10 is reached, in which the cutting points of the two blades 7 and 9 are touching. A continuous wedge-like cut has been created in the eye by device 1 and a complementary ring R of corneal tissue (see FIG. 9) has been removed. The adjacent walls of the cut are then sutured together in order to achieve the desired flattening of the corneal surface.

Numerous other cutting device embodiments fall within the contemplated scope of the present invention. Thus, for example, the cutting device may include a means for adjusting the angle between the cutting directions of the two cutting means (which may be cutting blades, laser knives, electrosurgical knives or other cutting means). Furthermore, the cutting directions of the two cutting means may be parallel rather than mutually angulated. Alternative means for positively limiting incision depths, such as other configurations of mechanical stops, may be provided. No pronounced design variations are necessary when the cutting means are laser knives; a gross adjustment means such as provided by adjustment screw 33 should be included, but a fine adjustment means such as provided by adjustment screw 71 will typically not be needed.

A cutting device of the present invention may be employed in a surgical procedure for the correction of hyperopia. In this clinical situation a 360° closed wedge-like cut is created that is generally triangular in transverse cross-section, but with the narrowest part of the cut being at the outer corneal surface and the base of the generally triangular cut being within the cornea (the cut should not reach the Descemet's membrane) and forming the bottom of the cut (see FIG. 17). It is necessary, in order to form the two sides of such a cut, that the cutting directions of the two cutting means cross one another, as viewed in the plane of FIG. 10. When the cutting means are cutting blades, it is necessary for one blade to be in a leading position with respect to the other (trailing) blade so that the two blades can cross one another when they are advanced into the corneal tissue (e.g. by the rotation of an adjustment screw such as screw 71). After the two sides of the wedge-like cut depicted in FIG. 17 have been made, the bottom of the cut is made and the complementary ring of corneal tissue removed (for example with the use of a conical end mill). The two side walls of the cut are then sutured together. This causes a controlled flattening of the inner corneal surface, which in turn gives rise to an anterior displacement of the focal point.

I claim:

1. An ophthalmic device for simultaneously forming two incisions oriented at an angle with respect to one another along a generally annular pat on an eye, said device comprising:
   a base;
   means connected to the base to conform and secure the eye and the ophthalmic device to one another;
   pattern means for defining said generally annular path;
   rotation means adapted to be disposed and rotated on the base; and
   first and second cutting means fixedly connected generally adjacent one another at generally the same location along said path, said first and second cutting means being angularly aligned to one another for making a generally wedge shaped incision in said eye at said same location thereon, said first and second cutting means being operatively connected to said pattern means and said rotation means such that said rotation means moves said generally adjacent first and second cutting means from said same location and simultaneously along the generally annular path defined by the pattern means, such that said first and second cutting means remain generally adjacent one another at all respective locations along the path on the eye, whereby the generally adjacent alignment of the first and second cutting means at all locations along said path enables an accurate wedge shaped generally annular incision of the eye.

2. A device of claim 1 wherein said first and second cutting means are mounted upon said rotation means in such a manner that the distance between the locus of tissue being cut by the first cutting means and the locus of tissue being cut at the same time by the second cutting means is substantially equal to the distance between said two incisions.

3. A device of claim 2 wherein each of said first and second cutting means comprises a cutting blade having a cutting edge terminating at a cutting point, with said cutting blades being securely ganged together with said cutting edges oriented at an acute angle with respect to one another.

4. A device of claim 3 wherein said mounting means comprises a means for adjusting the position of said two ganged cutting blades with respect to the surface of the patient's eye without effecting a relative movement between said two blades.

5. A device of claim 4 wherein said mounting means further comprises a means for simultaneously and progressively advancing said two ganged cutting blades, while maintaining said cutting edges oriented at said acute angle with respect to one another, to a position in which said cutting points are touching one another, whereby said two incisions can form a wedge-like cut of eye tissue along said path.

6. A device of claim 1 wherein said path is predetermined by said pattern means prior to the commencement of the formation of said two incisions.

7. A device of claim 6 wherein said pattern means comprises a generally annular cam operatively connected to said base, and said rotation means is adapted to operatively engage said cam, whereby said first and second cutting means both follow a predetermined path related to the shape of said cam as the rotation means is rotated on the base.

8. A device of claim 7 wherein said cam is removable from and replaceable on said base, whereby said path can be varied by removing and replacing said cam with a different generally annular cam having a different shape.

9. Device of claim 1 wherein each of said first and second cutting means comprises a cutting blade.

10. A device of claim 1 wherein each of said first and second cutting means comprises a laser knife.

11. A device of claim 1 wherein each of said first and second cutting means comprises a heated electrosurgical knife.

12. A device of claim 1 wherein said pattern means includes a feedback mechanism capable of altering the incision path as the cutting operation is in progress.

13. A device of claim 1 further comprising means to positively limit the depths of said two incisions.

14. A device of claim 1 wherein the generally adjacent first and second cutting means are disposed such that said first cutting means is in a leading cutting position at the generally same location along said path on the eye.

* * * * *